United States Patent [19]

Katsuragi

[11] Patent Number: 4,944,303
[45] Date of Patent: Jul. 31, 1990

[54] NONCONTACT TYPE TONOMETER
[75] Inventor: Kenjiro Katsuragi, Tokyo, Japan
[73] Assignee: Topcon Corporation, Tokyo, Japan
[21] Appl. No.: 137,611
[22] Filed: Dec. 24, 1987
[30] Foreign Application Priority Data Dec. 27, 1986 [JP] Japan .................................. 61-311257
May 21, 1987 [JP] Japan .................................. 62-124165

[51] Int. Cl.$^5$ ............................................. A61B 3/16
[52] U.S. Cl. ..................................... 128/648; 128/652
[58] Field of Search ................................ 128/645, 648

[56] References Cited
U.S. PATENT DOCUMENTS

| | | | |
|---|---|---|---|
| 3,756,073 | 9/1973 | Lavallee et al. ..................... | 128/648 |
| 3,832,890 | 9/1974 | Grolman et al. ..................... | 128/648 |
| 4,665,923 | 5/1987 | Kobayashi .......................... | 128/648 |
| 4,705,045 | 11/1987 | Nishimura ........................... | 128/648 |
| 4,724,843 | 2/1988 | Fisher .................................. | 128/648 |

FOREIGN PATENT DOCUMENTS 183621  6/1986  European Pat. Off. ............ 128/648

Primary Examiner—Max Hindenburg
Assistant Examiner—John P. Lacyk
Attorney, Agent, or Firm—Finnegan, Henderson, Farabow, Garrett & Dunner

[57] ABSTRACT

A noncontact type tonometer, in which an axial line extending in the direction of air pulse projected by an air pulse projecting nozzle towards a cornea of an eye to be tested is coaxial with an optical axis of an alignment optical system for verifying an alignment with respect to a vertex of the cornea, includes an anterior portion observing system capable of optically observing an anterior portion of the eye and having an optical axis coaxial at least with a part of the optical axis of the alignment optical system.

24 Claims, 2 Drawing Sheets

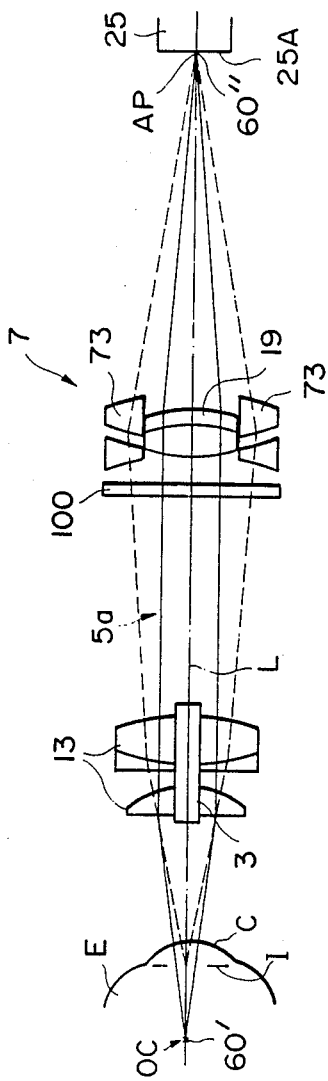
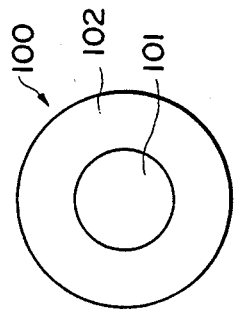
F I G. 2(a)
F I G. 2(b)

NONCONTACT TYPE TONOMETER

BACKGROUND OF THE INVENTION

1. Field of the Invention

This invention relates to a noncontact type tonometer for measuring eye pressure by projecting fluid towards a cornea.

2. Prior Art of the Invention

As a tonometer of this type, an air puff type tonometer is known, for example. In this conventional tonometer, various alignment works must be performed before measurement, such as, for example, alignment of a working position of a main instrument and a vertical or horizontal position thereof with respect to an eye to be tested.

Subsequently, an air pulse is projected towards the cornea of the eye to be tested through an air pulse projecting nozzle, and light is projected towards the cornea by a light projector.

Then, the projected light is reflected off the cornea, and, when the light quantity entering into a light receiving device becomes maximum, the fact that the cornea has been made applanated by the air pulse is confirmed and the measurement is finished.

However, in a conventional tonometer of this type, the examiner is busy in observing an optically enlarged corneal portion during alignment verification and measurement and, therefore, is unable to observe the entire eye to be tested. Therefore, the examiner does not know the state of the eye under which the measurement is being carried out.

Therefore, even if the light projected by the light projector is reflected by an anterior portion of the eye and enters into the light receiving device, when, for example, an eyelash or an eyelid (anterior portion) hangs over the eye to be tested and by this reason, the light quantity received by the light receiving device becomes maximum, there is a risk that examiner may overlook it. Thus, the conventional tonometer is problematical in reliability and accuracy of measurement.

SUMMARY OF THE INVENTION

An object of the present invention is to provide a noncontact type tonometer, in which an anterior portion of an eye to be tested can be observed.

Another object of the invention is to provide a noncontact type tonometer, in which an eye to be tested can be observed through a monitor.

A further object of the invention is to provide a noncontact type tonometer, in which an image of an anterior portion and an alignment target mark image are not affected by a flare of the other image.

A feature of the present invention is that a noncontact type tonometer, in which an axial line of an air pulse projection nozzle is coaxial with an optical axis of an alignment optical system, comprises an anterior portion observing system having an optical axis which becomes coaxial with at least a part of an optical axis of an alignment optical system, and which is provided so that an anterior portion can be observed.

Another feature of the present invention is that an anterior portion observing system has a TV camera placed at an imaging position of an optical system so that an eye to be tested can be monitored.

A further feature of the present invention is that the wavelength of light emitted by a light source of an anterior portion observing system is different from that of the light emitted from a light source of an alignment optical system so that an image of an anterior portion and an alignment target mark image are not affected by a flare of the other image.

The above-mentioned and other objects, characteristic features and advantages of the present invention will become more apparent to those skilled in the art as the disclosure is made in the following description of the preferred embodiments of the invention, as illustrated in the accompanying drawings.

BRIEF DESCRIPTION OF THE DRAWINGS

FIG. 2(A) is an optical arrangement of an important portion of a noncontact type tonometer according to a second embodiment of the present invention; and FIG. 2(B) is a plan view showing the structure of a filter used in the second embodiment.

DETAILED DESCRIPTION OF THE PREFERRED EMBODIMENT

Figure 1:
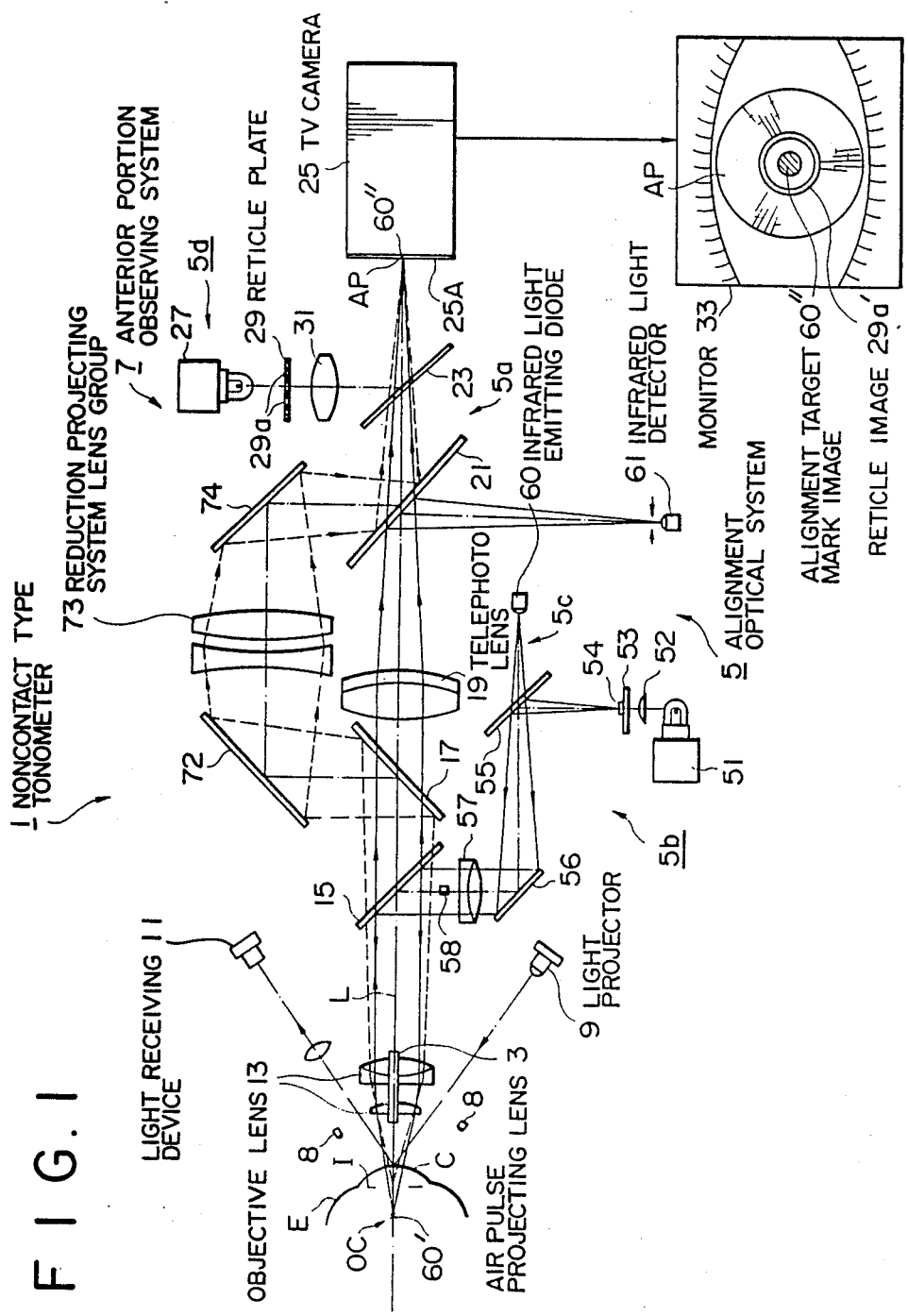
FIG. 1 is an optical arrangement of a noncontact type tonometer according to a first embodiment of the present invention.

A noncontact type tonometer according to a first embodiment of the present invention will be described hereunder with reference to the accompanying drawings.

In FIG. 1, a noncontact type tonometer 1 is a so-called air puff type tonometer and comprises an air pulse projecting nozzle 3 capable of projecting air pulse towards a cornea C of an eye E to be tested, an alignment optical system 5 for carrying out an alignment verification, and an anterior portion observing system capable of optically observing the anterior portion of the eye E.

And, a projector 9 for projecting light towards the cornea C during eye pressure measurement and a light receiving device 11 for receiving the light projected by the projector 9 and reflected by the cornea C are disposed at both sides of an axial line L of the air pulse nozzle 3, with the axial line L placed therebetween, and a pair of light sources 8 for emitting visual light for illuminating the anterior portion are disposed at both sides of the axial line L.

The alignment optical system 5 can be divided broadly into an alignment light image receiving optical system 5a, a sight fixation mark projecting system 5b, an alignment light projecting system 5c, and a reticle projecting system 5d.

And, in the alignment light image receiving optical system 5a, an optical axis thereof is disposed coaxial with the axial line L of the air pulse projecting nozzle 3, and an objective lens 13, a half mirror 15, a dichroic mirror 17, a telephoto lens 19 and two dichroic mirrors 21 and 23 are arranged in this order and in such a manner as that one placed nearer to the eye E comes first.

The dichroic mirrors 17 and 23 reflect visible light and allows to pass infrared light pass therethrough, whereas the dichroic mirror 21 reflects visible light and acts as a half mirror for infrared light.

In the sight fixation mark projecting system 5b, a part of an optical axis thereof is disposed coaxial with an optical axis of the alignment light image receiving optical system 5a, the light coming from a visual light source 51 is condensed by a condenser lens 52 to illuminate a sight fixation mark 54 formed on a sight fixation mark plate 53.

And, the light coming from the sight fixation mark plate 54 is reflected by a dichroic mirror 55 of the type which reflects visible light and allows infrared light to pass therethrough, and thereafter, is reflected by the half mirror 15 through a collimator lens 57 to become a collimated beam of light, and projected towards the eye E after passing through the air pulse projecting nozzle 3.

In case the eye E suffers from a myopia or a hyperpia, a diopter correcting lens 58 is disposed within an optical path of the sight fixation mark projecting system 5b.

Further, most of the component elements of the alignment light projecting system 5c are common with those of the sight fixation mark projecting system 5b.

That is, the light emitted by an infrared emission diode 60 as an alignment target mark, passes through the dichroic mirror 55 and then, is projected towards the cornea C through mirror 56, collimater lens 57, half mirror 15 and objective lens 13.

At that time, a virtual image 60' of the alignment target mark 60 is formed at the center OC of curvature of the cornea C by the objective lens 13.

And, the target mark light reflected by the cornea C moves backwardly on the projecting optical path of the alignment target mark in a manner as if it were emitted by the virtual image 60', then is made into parallel pencil of light rays by the objective lens 13, then passes through the half mirror 15, dichroic mirror 17, telephoto lens 19, and dichroic mirrors 21 and 23, and then reaches a photosensitive surface 25A of the TV camera 25.

Therefore, an image 60" of the alignment target mark is formed on the photosensitive surface 25A by the telephoto lens 19 and displayed on the monitor 33.

When the alignment target mark light reflected on the infrared half mirror surface of the dichroic mirror 21, is detected by an infrared light detector 61 after the alignment is completed, a working trigger signal fed to an air puff projecting system, known per se, is generated.

Next, in the reticle projecting system 5d, a part of the optical axis thereof is in alignment with the optical axis of the alignment light image receiving optical system 5a and the light emitted by the visible light source 27 illuminates the reticle plate 29 having an annular reticle target mark 29a.

And, the light passed through the reticle target mark 29a is imaged on the photosensitive surface 25A of the TV camera 25 by the imaging lens 31 after being reflected by the dichroic mirror 23. The image formed on the photosensitive surface 25A is displayed on the monitor 33 as a reticle image 29a'.

The alignment work is performed by moving the whole equipment vertically and/or horizontally so that the alignment target image 60" is brought to the center of the reticle image 29a' of the monitor 33. Similarly, the working distance (distance between the air pulse projecting nozzle 3 and the cornea C) is adjusted by moving the whole equipment forward and backward so that the alignment target mark image 60" becomes sharp.

Herein, in the anterior portion observing system 7, a part of the optical axis thereof is coaxial with the axial line L of the air pulse projecting nozzle 3. Accordingly, a part of the optical axis of the anterior portion observing system 7 is coaxial with a part of the optical axis of the alignment optical system 5.

And, the anterior portion observing system 7 comprises an objective lens 13, a dichroic mirror 17 disposed between a half mirror 15 and a telephoto lens 19, a mirror 72 disposed on the reflecting optical axis of the dichroic mirror 17, a reduction projecting system lens group 73, a mirror 74, and a dichroic mirror 21.

The reduction projecting system lens group 73 is constructed as such that the anterior portion of the eye E, particularly the image of an iris I thereof is imaged, in a reduced scale, on the photosensitive surface 25A of the TV camera 25 through the objective lens 13.

Therefore, the visible light reflected on the anterior portion which is illuminated by the light source 8, is condensed by the objective lens 13, then passes through the half mirror 15, and then reflected by the dichroic mirror 17 and the mirror 72 in this order.

After passing through the reduction projecting system lens group 73, the reflection light is reflected by the mirror 74 and the dichroic mirror 21. Therefore, when the reflection light passes the dichroic mirror 23, it is imaged on the photosensitive surface 25A by the function of the reduction projecting system lens group 73 and the image (anterior portion image) AP is displayed on the monitor 33.

Next, a noncontact type tonometer according to a second embodiment of the present invention will be described with reference to the accompanying drawings.

As apparent from FIG. 2(a), in this embodiment, both optical axes of the alignment light image receiving optical system 5a and the anterior portion observing optical system 7 are coaxial with each other over the entire length of the optical path.

In the figure, identical parts of FIG. 1 are denoted by identical reference numerals and description thereof is omitted.

In this embodiment, the reduction projection system lens group 73 of the anterior portion observing system 7 is formed in an annular shape. Within a space formed at an inner periphery side thereof, a telephoto lens 19 of the alignment light image receiving optical system 5a is contained.

A wavelength selecting filter 100 is disposed in front of the reduction projecting system lens group 73 and the telephoto lens 19. The wavelength selecting filter 100, as shown in FIG. 2(b), comprises a central portion 101 which allows infrared light as the alignment target image light to pass therethrough and blocks visible light as the anterior portion observing light, and a peripheral portion 102 which blocks the alignment target image light and allows the anterior portion observing light to pass therethrough.

Therefore, after passing through the objective lens 13, the light coming from the anterior portion of the eye E passes only through the peripheral portion 102 of the wavelength selecting filter 100 and then enters into the reduction projecting lens group 73. As a result, an anterior portion image AP is formed on the photosensitive surface 25A.

On the other hand, after passing through the objective lens 13, the alignment target mark light passes only through the central portion 101 of the wavelength selecting filter 100 and then is imaged, as an alignment target mark image 60", on the photosensitive surface 25A by the telephoto lens 19.

As described in the foregoing, in the first and second embodiments, by projecting the whole image of the eye E onto the photosensitive surface 25A by means of the anterior portion observing system 7, alignment verification, eye pressure measurement, etc. can be performed while observing the anterior portion of the eye E, too.

Therefore, since the alignment verification and eye pressure measurement can be performed properly, the reliability and accuracy of the eye pressure measurement are improved.

Further, since the eye E can be observed through the monitor 33, it is no more necessary that examiner performs such a work as focussing during the alignment verification while observing the eye E very carefully through an ocular as he did. Therefore, irregularity of a measuring value caused by eye fatigue of examiner, for example, can be prevented from occurring.

Furthermore, the wavelength of the alignment target mark light is different from that of the anterior portion observing light, and each alignment light image receiving optical system 5a and anterior portion observing system 7 has an optical wavelength selectivity.

Therefore, the anterior portion image AP is imaged on the photosensitive surface 25A only by the anterior portion observing system 7, whereas the alignment target mark image 60" is imaged thereon only by the alignment light image receiving optical system 5a.

As a result, since the anterior portion image A and alignment target mark image 60" are not affected by a flare of the other image, the anterior portion image AP and alignment target mark image 60" displayed on the monitor 33 become very clear.

Obviously, many variations and modifications of the present invention can be made in light of the above teachings. It is therefore to be understood that within the scope of the appended claims, the present invention may be practiced otherwise than as specifically described herein.

What is claimed is:

1. A noncontact type tonometer having an orifice tube for discharging a fluid to deform a cornea of an eye under test and an alignment optical system for aligning an axis of the orifice tube with the cornea and viewing the anterior portion of the eye under test, said alignment optical system comprising:
   an orifice tube disposed along an axis;
   projection means for projecting an alignment target mark onto the cornea of the eye under test, the alignment target mark including light of a first range of wavelengths;
   illumination means for illuminating an anterior portion of the eye under test with light of a second range of wavelengths different from said first range of wavelengths;
   first imaging optical means, having a first optical axis coaxial with the axis of the orifice tube, for forming an image of the alignment target mark on a plane and for passing light of the first range of wavelengths;
   second imaging optical means for forming an image of the anterior portion of the eye on the plane and for passing light of the second range of wavelengths; and
   reticle means for providing a reticle image on the plane, the relative positions between the reticle image and at least one of (i) the image of the alignment target and (ii) the image of the anterior portion of the eye formed on the plane being indicative of the relative positions of the axis of the orifice tube and the cornea.

2. A non-contact tonometer as claimed in claim 1, wherein the reticle is an image of a reticle plate projected onto the plane.

3. A non-contact tonometer as claimed in claim 1, wherein the reticle formed on the plane is co-axial with the first optical axis.

4. A non-contact tonometer as claimed in claim 1, wherein said first range of wavelengths is in the infrared range.

5. A non-contact tonometer as claimed in claim 4, wherein said second range of wavelengths is in the visible range.

6. A non-contact tonometer as claimed in claim 1, wherein said second imaging optical means includes a first dichroic mirror disposed along said first optical axis for passing light in said first range of wavelengths and reflecting light in said second range of wavelengths along a second optical path, a second dichroic mirror for passing light in said first range of wavelengths and reflecting light in said second range of wavelengths along said first optical axis, and at least one mirror for reflecting light in said second range of wavelengths emanating from said first dichroic mirror to said second dichroic mirror.

7. A non-contact tonometer as claimed in claim 6, further including a reduction projecting system lens group disposed between said first and second dichroic mirrors for forming a reduced image of the anterior portion of the eye on the plane.

8. A non-contact tonometer as claimed in claim 7, wherein the first imaging optical means includes an objective lens for collimating light reflected from the cornea and a telephoto lens for forming the image of light rays reflected from the cornea onto the plane disposed along the first optical axis, the first dichroic mirror being disposed between the objective lens and the telephoto lens.

9. A non-contact tonometer as claimed in claim 8, wherein said first range of wavelengths is in the infrared range.

10. A non-contact tonometer as claimed in claim 9, wherein said second range of wavelengths is in the visible range.

11. A non-contact tonometer as claimed in claim 1 wherein said second imaging optical means includes an annular lens disposed along the first optical axis for forming a reduced image of the anterior portion of the eye on the plane and an annular filter disposed between the cornea of the eye under test and the annular lens for passing only light in said second range of wavelengths to the annular lens.

12. A non-contact tonometer as claimed in claim 11, wherein the first imaging optical means includes an objective lens for collimating light reflected from the cornea and a telephoto lens for forming the image of light rays reflected from the cornea on the plane disposed along the first optical axis, the annular lens being disposed about the objective lens.

13. A non-contact tonometer as claimed in claim 12, wherein said first range of wavelengths is in the infrared range.

14. A non-contact tonometer as claimed in claim 13, wherein said second range of wavelengths is in the visible range.

15. A non-contact tonometer as claimed in claim 4, further including TV camera means having sensitivity in the infrared range for converting an infrared image of the alignment target mark into an electronic signal, the electronic signal being capable of being converted into a visible image by a TV monitor.

16. A non-contact tonometer as claimed in claim 9, further including TV camera means having sensitivity in the infrared range for converting an infrared image of the alignment target mark into an electronic signal, the electronic signal being capable of being converted into a visible image by a TV monitor.

17. A non-contact tonometer as claimed in claim 13, further including TV camera means having sensitivity in the infrared range or converting an infrared image of the alignment target mark into an electronic signal, the electronic signal being capable of being converted into a visible image by a TV monitor.

18. A non-contact type tonometer having an orifice tube for discharging a fluid to deform a cornea of an eye under test and alignment optical system for aligning an axis of the orifice tube with the cornea and viewing the anterior portion of the eye under test, said alignment optical system comprising:
   an orifice tube disposed along an axis;
   projection means, having an optical axis, at least a part of which is coaxial with the axis of the orifice tube, for projecting an alignment target mark onto a cornea of the eye under test, the alignment target mark including light of a first range of wavelengths;
   illumination means illuminating an anterior portion of the eye under test with light of a second range of wavelengths different from said first range of wavelengths;
   first imaging optical means, having a first optical axis coaxial with the axis of the orifice tube, for forming an image of the alignment target mark on a plane and for passing light of the first range of wavelengths;
   second imaging optical means, having an optical axis at least a part of which is coaxial with the axis of the orifice tube, for forming an image of the anterior portion of the eye on the plane and for passing light of the second range of wavelengths; and
   reticle means for providing a reticle image on the plane, the relative positions between the reticle image and at least one of (i) the image of the alignment target and (ii) the image of the anterior portion of the eye formed on the plane being indicative of the relative positions of the axis of the orifice tube and cornea.

19. A non-contact type tonometer as claimed in claim 18, wherein said first imaging optical means includes an objective lens for collimating light reflected from the cornea and a telephoto lens for forming the image of light rays reflected from the cornea onto the plane disposed along the first optical axis, wherein said second imaging optical means includes:
   a first dichroic mirror disposed between said objective lens and said telephoto lens for passing light in said first range of wavelengths and reflecting light in said second range of wavelengths along a second optical path;
   a second dichroic mirror disposed along said first optical
   axis for passing light in said first range of wavelengths and reflecting light in said second range of wavelengths along said first optical axis;
   at least one mirror for reflecting light in said second range of wavelengths emanating from said first dichroic mirror to said second dichroic mirror; and
   a reduction projecting system lens group disposed between said first and second dichroic mirrors for forming a reduced image of the anterior portion of the eye on the plane.

20. A non-contact type tonometer as claimed in claim 19, wherein said first range of wavelengths is in the infrared range and said second range of wavelengths is in the visible range.

21. A non-contact type tonometer as claimed in claim 20, further including TV camera means having sensitivity in the infrared range for converting an infrared image of the alignment target mark into an electronic signal, the electronic signal being capable of being converted into a visible image by a TV monitor.

22. A non-contact type tonometer as claimed in claim 18, wherein said first imaging optical means includes an objective lens for collimating light reflected from the cornea and a telephoto lens for forming the image of light rays reflected from the cornea onto the plane disposed along the first optical axis, wherein said second imaging optical means includes;
   an annular lens disposed about said object lens of said first imaging optical means; and
   an annular filter disposed between the cornea of the eye under test and said annular lens for passing only light in said second range of wavelengths to said annular lens.

23. A non-contact type tonometer as claimed in claim 22, where said first range of wavelengths is in the infrared range and said second range of wavelengths being in the visible range.

24. A non-contact type tonometer as claimed in claim 23, further including TV camera means having sensitivity in the infrared range for converting an infrared image of the alignment target mark into an electronic signal, the electronic signal being capable of being converted into a visible image by a TV monitor.

* * * * *

UNITED STATES PATENT AND TRADEMARK OFFICE
CERTIFICATE OF CORRECTION

PATENT NO. : 4,944,303
DATED : July 31, 1990
INVENTOR(S) : Kenjiro Katsuragi

It is certified that error appears in the above-identified patent and that said Letters Patent is hereby corrected as shown below:

At column 6, line 59, change "!2" to --12--.

Signed and Sealed this

Twenty-fourth Day of September, 1991

Attest:

HARRY F. MANBECK, JR.

Attesting Officer

Commissioner of Patents and Trademarks